United States Patent [19]
Granger et al.

[11] Patent Number: 5,536,740
[45] Date of Patent: Jul. 16, 1996

[54] SKIN CARE COMPOSITIONS CONTAINING DIMETHYL IMIDAZOLIDINONE AND RETINOL OR RETINYL ESTER

[75] Inventors: Stewart P. Granger, Paramus; Anthony V. Rawlings, Wyckoff; Ian R. Scott, Allendale, all of N.J.

[73] Assignee: Elizabeth Arden Company, Division of Conopco, Inc., New York, N.Y.

[21] Appl. No.: 457,900

[22] Filed: Jun. 1, 1995

[51] Int. Cl.$^6$ .................... A61K 31/415; A61K 31/215; A61K 31/07

[52] U.S. Cl. .................... 514/392; 514/529; 514/549; 514/725

[58] Field of Search .................... 514/392, 529, 514/725, 549

[56] References Cited

U.S. PATENT DOCUMENTS

| | | | |
|---|---|---|---|
| 4,216,201 | 8/1980 | Calvo | 424/63 |
| 4,900,550 | 2/1990 | Lowry | 424/195 |
| 5,124,320 | 6/1992 | Ivy et al. | 514/159 |

FOREIGN PATENT DOCUMENTS

| | | |
|---|---|---|
| 2101101 | 2/1994 | Canada. |
| WO93/19743 | 10/1993 | WIPO. |

OTHER PUBLICATIONS

Vahlquist A. et al., "Isotretinoin Treatment of Severe Acne Affects the Endogenous Concentration of Vitamin A in Sebaceous Glands", *J. Invest. Dermatol.*, vol. 94, (1990), pp. 496–498.

Ellis, C. N. et al., "Treatment of Actinically Aged Skin with Topical Tretinoin", *Pharmacology of Retinols in Skin*, vol. 3, (1989), pp. 249–252.

Lowe, N. J. et al., "Systemic Reinoids in Psoriasis: Comparative Efficacy and Toxicity", *Pharmacology of Retinols in Skin*, vol. 3, (1989), pp. 240–248.

*Primary Examiner*—Phyllis G. Spivack
*Attorney, Agent, or Firm*—Rimma Mitelman

[57] ABSTRACT

Dimethyl imidazolidinone in combination with either retinol or retinyl ester resulted in a synergistic enhancement in keratinocyte proliferation and synergistic inhibition of keratinocyte differentiation. The effects of the retinol or retinyl esters in combination with dimethyl imidazolidinone were analogous to treatment with retinoic acid.

5 Claims, No Drawings

SKIN CARE COMPOSITIONS CONTAINING DIMETHYL IMIDAZOLIDINONE AND RETINOL OR RETINYL ESTER

FIELD OF THE INVENTION

BACKGROUND OF THE INVENTION

Retinol (vitamin A) is an endogenous compound which occurs naturally in the human body and is essential for normal epithelial cell differentiation. Natural and synthetic vitamin A derivatives have extensively been used in the treatment of a variety of skin disorders and have been used as skin repair or renewal agents. Retinoic acid has been employed to treat a variety of skin conditions, e.g., acne, wrinkles, psoriasis, age spots and discoloration. See e.g., Vahlquist, A. et al., *J. Invest. Dermatol.*, Vol. 94, Holland D. B. and Cunliffe, W. J. (1990), pp. 496–498; Ellis, C. N. et al., "Pharmacology of Retinols in Skin", Vasel, Karger, Vol. 3, (1989), pp. 249–252; Lowe, N. J. et al., "Pharmacology of Retinols in Skin", Vol. 3, (1989), pp. 240–248; PCT Patent Application No. WO 93/19743. Retinol and retinyl esters, such as retinyl acetate and retinyl palmitate, are easier to formulate/stabilize than retinoic acid. Unfortunately, retinol and retinyl esters are less effective than retinoic acid at providing skin benefits. The present invention is based, in part, on the discovery that certain combinations of retinol or retinyl esters with dimethyl imidazolidinone result in a synergistic improvement in keratinocyte proliferation and differentiation. The effects of dimethyl imidazolidinone combined with retinol or a retinyl ester were analogous to the effects of retinoic acid. Thus, a mixture of fatty acid amides with retinol or retinyl esters mimics retinoic acid yet is easier to use than retinoic acid.

Dimethyl imidazolidinone is currently used in cosmetic products to combat bacterial contamination. The art does not disclose, however, skin conditioning compositions based on synergistic combinations of dimethyl imidazolidinone with retinol or a retinyl ester. None of the art cited above addresses the need for an effective alternative to retinoic acid.

Accordingly, it is an object of the present invention to provide a skin conditioning composition containing a combination of retinol or a retinyl ester with dimethyl imidazolidinone.

It is another object of the invention to provide a method of conditioning skin with a composition containing as an active system a mixture of dimethyl imidazolidinone with retinol or a retinyl ester.

It is yet another object of the invention to provide a substitute for retinoic acid in cosmetic compositions.

These and other objects of the invention will become more apparent from the detailed description and examples that follow.

SUMMARY OF THE INVENTION

The above objects are attained by the present invention which includes, in part, a skin conditioning composition containing:

(a) from about 0.001% to about 10% of retinol or a retinyl ester;

(b) from about 0.01% to about 10% of dimethyl imidazolidinone; and (c) a cosmetically acceptable vehicle.

The term "conditioning" as used herein means prevention and treatment of dry skin, photodamaged skin, appearance of wrinkles, age spots, aged skin, increasing stratum corneum flexibility, and generally increasing the quality of skin. The composition may be used to improve skin desquamation and epidermal differentiation.

The presence of dimethyl imidazolidinone in the inventive product substantially improves the performance of retinol or a retinyl ester, i.e., dimethyl imidazolidinone substantially increases the ability of retinol or a retinyl ester to affect cellular proliferation and differentiation. Dimethyl imidazolidinone has no or little effect on improving skin benefit when used alone; a substantial increase in skin benefit is only realized when dimethyl imidazolidinone is combined with retinol or a retinyl ester. In short, the present invention is based, at least in part, on the discovery of synergistic interaction between retinol or a retinyl ester and dimethyl imidazolidinone.

By virtue of including dimethyl imidazolidinone into compositions containing retinol or a retinyl ester, the performance of the compositions is substantially improved. Alternatively, lower levels of retinol or a retinyl ester may be included in the composition containing dimethyl imidazolidinone to equal the performance of a similar formulation without dimethyl imidazolidinone.

DESCRIPTION OF THE PREFERRED EMBODIMENT

The inventive compositions contain, as a first essential ingredient, a compound selected from the group consisting of retinol or a retinyl ester. The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its ready commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate.

The preferred ester for use in the present invention is selected from retinyl palmitate, retinyl acetate and retinyl propionate, because these are the most commercially available and therefore the cheapest.

Retinol or retinyl ester is employed in the inventive composition in an amount of from about 0.001% to about 10%, preferably in an amount of from about 0.01% to about 1%, most preferably in an amount of from about 0.01% to about 0.5%.

The second essential ingredient of the inventive compositions is dimethyl imidazolidinone. It has the following formula:

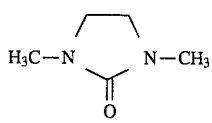

Dimethyl imidazolidinone is included in the inventive compositions in an amount ranging from about 0.001% to about 10%, preferably from about 0.01% to about 1%, most preferably from about 0.1% to about 0.5%.

The ratio of retinol or a retinyl ester to dimethyl imidazolidinone in the inventive compositions is generally in the range of from about 500:1 to about 1:500, preferably in the range of from about 60:1 to about 1:160.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Actives are defined as skin benefit agents other than emollients and other than ingredients that merely improve the physical characteristics of the composition. Although not limited to this category, general examples include sunscreens and tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic acid, columbinic acid, eicosa-(n-6,9,13)-trienoic acid, arachidonic acid, γ-linolenic acid, timnodonic acid, hexanoic acid and mixtures thereof.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

Use of the Composition

The composition according to the invention is intended primarily as a product for topical application to human skin, especially as an agent for conditioning and smoothening of the skin, and preventing or reducing the appearance of wrinkled or aged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin and/or hair treatment composition of the invention can be formulated as a lotion having a viscosity of from 4,000 to 10,000 mPas, a fluid cream or gel having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a capsule or a bottle or a roll-ball applicator or a propellant-driven aerosol device or a container fitted with a pump suitable for finger operation. When the composition is a cream, it can simply be stored in a capsule or a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

MATERIALS AND METHODS

Cell Culture

Human keratinocytes, isolated from neonatal foreskin by trypsin treatment were grown in Dulbecco Modification Eagle (DME) Hams F12 (1:1) medium/10% fetal calf serum in the presence of irradiated 3T3 mouse fibroblasts for establishing dividing keratinocyte colonies. Cells were grown under the above condition until their second passage and kept frozen for future use. Frozen second passage keratinocytes were thawed and plated into the above medium and grown for five days before they were switched to a serum-free MCDB 153-based medium keratinocyte growth medium (KGM) from Clonetics Corporation, San Diego, Calif., containing 0.15 mM Ca; or keratinocyte serum-free media (KSFM) from GIBCO containing 0.09 mM Ca). On day 7, when the cells were 80–90% confluent, they were trypsinized and plated in the serum-free medium for the various experiments.

Thymidine Assay $^3$H-Thymidine Incorporation and Keratinocyte Proliferation

The incorporation of $^3$H-thymidine by cultured keratinocytes was used as an assay of keratinocyte proliferation. Thymidine is one of four deoxynucleosides which are the monomeric units of DNA, the universal library of genetic information in the animal kingdom. Prior to cell division of a somatic cell such as a keratinocyte, the complete genome of the cell undergoing cell division is replicated. This involves large scale DNA synthesis by the cell and enables both daughter cells to receive identical copies of the genetic material. When $^3$H-thymidine is included in the culture media of keratinocytes which are synthesizing DNA in preparation for cell division then the labelled nucleoside is incorporated into the newly synthesized DNA. The extent of incorporation of $^3$-thymidine into a population of cells is proportional to the rate of DNA synthesis by this population of cells and therefore an indication of their cellular proliferation.

Keratinocytes (that were cultured as described above) were plated in 24 well plates at a density of 40,000 cells per well in 1 ml media. After incubation for four days or until the cells were 60–70% confluent, the media was changed. Test compounds were added (in triplicate) to the wells 24 hours after the media change, and four hours later 1 µCi$^3$H-Thymidine in 50 µl media was added per well. Cells were incubated for a further 24 hours. Media was removed from the cells, 10% ice cold trichloroacetic acid (TCA) added and plates were incubated on ice for 30 minutes. Cells were washed five times with 5% TCA and allowed to dissolve in 500 µl 0.1M NaOH for at least one hour (usually overnight). The preparations were neutralized with 0.1M HCl; 50 µl of the cell preparation was used to determine total protein content. Disintegrations per minute (DPM) from a H labelling of DNA was determined by liquid scintillation counting of 900 µl of the cell preparation. Thymidine incorporation results were expressed as DPM/µg protein.

Transglutaminase Assay

Transglutaminase Assay and Keratinocyte Differentiation

During the process of terminal differentiation in the epidermis, a 15 nm thick layer of protein, known as the cornified envelope (CE) is formed on the inner surface of the cell periphery. The CE is composed of numerous distinct proteins which have been cross-linked together by the formation of $N^\epsilon$-($\gamma$-glutamyl)lysine isodipeptide bonds catalyzed by the action of at least two different transglutaminases (TGases) expressed in the epidermis. TGase 1 is expressed in abundance in the differentiated layers of the epidermis, especially the granular layer, but is absent in the undifferentiated basal epidermis. Thus TGase I is a useful marker of epidermal keratinocyte differentiation with high TGase I levels indicating a more differentiated state. An ELISA based TGase I assay, using a TGase I antibody, was used to assess the state of differentiation of the cultured keratinocytes in the examples that follow.

Keratinocytes (cultured as described above) were plated in 96 well plates at a density of 3,000 cells per well in 200 µl media. After incubation for four days the media was changed to media containing test compounds (six replicates per test). The cells were cultured for a further 72 hours after which time the media was aspirated and the plates stored at −70° C. Plates were removed from the freezer, and the cells washed with PBS. 100 µl sterile water was added and the cells were freeze fractured by freezing at −70° C. then thawing. The cells were incubated for one hour at room temperature (R/T) with PBS/3% BSA (wash buffer, bovine serum albumin), then rinsed with a fresh aliquot of wash buffer. Cells were incubated with 50 µl of primary antibodies monoclonal anti-human transglutaminase (IgG) obtained from Amersham (mouse) diluted 1:300 in wash buffer for one hour, 37° C. then rinsed two times with wash buffer. Cells were then incubated with 50 µl of secondary antibody (Feb fragment, peroxidase conjugated anti-mouse IgG obtaining from Amersham) diluted 1:200 in wash buffer for one hour at 37° C., then rinsed two times with wash buffer. Cells were incubated with substrate solution (4 mg o-phenylene diamine and 3.3 µl 30% $H_2O_2$ in 10 ml 0.1M citrate buffer pH 5.0) for five minutes, R/T, in darkness (under aluminum foil). The reaction was stopped by the addition of 50 µl 4N $H_2O_4$. The absorbance of samples was read at 492 nm in the plate reader. Out of the six replicates, four were treated with both antibodies, two were treated only with the secondary antibody (i.e., to determine background binding of enzyme conjugated Ab). TGase levels were determined by subtracting background from the readings from each treatment and determining mean ±s.d. for the replicates exposed to both Ab.

DNA Assay

The level of TGase-1 detected after treatment of the cells could be influenced by cell number, i.e., the greater the number of cells the greater the level of TGase-1 detected. The level of TGase-1 was normalized to DNA content of the cells in the same well thus eliminating variation due to differences in cell number. DNA quantitation is a particularly useful indicator of cell number, including keratinocyte cell number, because each cell has to all intents and purposes an identical genome and therefore an identical quantity of DNA. The total DNA content of a well of cells therefore is directly proportional to the cell number in that well. Quantitation of DNA was used to normalize the TGase data to cell number.

Keratinocytes were plated in 96 well plates at a density of 3,000 cells per well in 2001 μl media. After incubation for four days the media was changed for media containing test compounds (6 replicates per test). The cells were cultured for a further 72 hours after which time the media was aspirated and the plates stored for at least 1.5 hours at −70° C. Plates were removed from the freezer, and the cells were fixed with cold 1:1 ethanol/acetone solution for 30 minutes. 100 μl/well of Hoechst dye (10 μg/ml final concentration) was added and this was incubated for 15 minutes, covered and then read in a fluorimeter (ex. 360 nm and em. 460 nm). The dye solution was removed and the wells were rinsed with PBS in preparation for the TGase assay.

EXAMPLE 1

Retinoic acid is more effective than retinol at altering keratinocyte differentiation state A. The effect on incorporation of $^3$H-thymidine/μg soluble protein 24 hours after the addition of retinoic acid and retinol at various concentrations was examined and the results are shown in Table 1A.

TABLE 1A

| Treatment | mean Thymidine incorp./μg protein ± s.d (% control) | p value vs Control | p value vs $10^{-7}$ROH | p value vs $10^{-8}$ROH | p value vs $10^{-9}$ROH |
|---|---|---|---|---|---|
| Control | 2094 ± 140 (100%) | — | 0.202 | 0.501 | 0.203 |
| 2.5 × $10^{-7}$M RA | 2475 ± 116 (118%) | 0.005 | 0.032 | 0.004 | 0.002 |
| 2.5 × $10^{-7}$M ROH | 2218 ± 73 (106%) | 0.202 | — | 0.021 | 0.005 |
| 2.5 × $10^{-8}$M RA | 2686 ± 72 (128%) | 0.001 | 0.001 | 0.001 | 0.001 |
| 2.5 × $10^{-8}$M ROH | 2034 ± 46 (97%) | 0.501 | 0.021 | — | 0.121 |
| 2.5 × $10^{-9}$M RA | 2556 ± 80 (122%) | 0.001 | 0.006 | 0.001 | 0.001 |
| 2.5 × $10^{-9}$M ROH | 1977 ± 19 (94%) | 0.203 | 0.005 | 0.121 | — | n = 3

All concentrations of retinoic acid tested, i.e., 2.5×$10^{-7}$M, 2.5×$10^{-8}$M and 2.5×$10^{-9}$M, significantly increased keratinocyte proliferation over both the ethanol control and each of the 2.5×$10^{-7}$M, 2.5×$10^{-8}$M and 2.5×$10^{-9}$M retinol treatments and they did so in a dose dependant manner. This is consistent with retinoic acid having a greater stimulatory effect on epithelial proliferation than retinol.

B. The effect on Transglutaminase levels normalized to DNA content of the cells after addition of retinoic acid and retinol was examined and the results are shown in Table 1B.

TABLE 1B

| Treatment | mean TGase/ DNA × $10^{-4}$ ± s.d (% control) | p value vs Control | p value vs $10^{-7}$ROH | p value vs $10^{-8}$ROH | p value vs $10^{-9}$ROH |
|---|---|---|---|---|---|
| Control | 2.44 ± 0.24 (100%) | — | 0.001 | 0.001 | 0.001 |
| 2.5 × $10^{-7}$M RA | 0.16 ± 0.11 (7%) | 0.001 | 0.001 | 0.001 | 0.001 |
| 2.5 × $10^{-7}$M ROH | 1.14 ± 0.22 (47%) | 0.001 | — | 0.001 | 0.001 |
| 2.5 × $10^{-8}$M RA | 1.34 ± 0.40 (55%) | 0.001 | 0.001 | 0.001 | 0.001 |
| 2.5 × $10^{-8}$M ROH | 1.89 ± 0.30 (77%) | 0.001 | 0.001 | — | 0.001 |
| 2.5 × $10^{-9}$M RA | 1.87 ± 0.49 (77%) | 0.001 | 0.001 | 0.784 | 0.001 |
| 2.5 × $10^{-9}$M ROH | 2.70 ± 0.59 (>100%) | 0.001 | 0.001 | 0.001 | — | n = 3

All concentrations of retinoic acid tested, i.e., 2.5×$10^{-7}$M, 2.5×$10^{-8}$M and 2.5×$10^{-9}$M decreased keratinocyte TGase level over both the ethanol control and did so to a significantly greater extent than each of the corresponding 2.5× $10^{-7}$M, 2.5×$10^{-8}$M and 2.5×$10^{-9}$M retinol treatments. The decrease in transglutaminase level was dose dependant for both retinoic acid and retinol. This is consistent with retinoic acid having a greater inhibitory effect on epithelial differentiation than retinol.

EXAMPLE 2

Dimethyl Imidazolidinone and Retinol Synergistically Enhanced Kerotinocyte Proliferation A. The effect on incorporation of $^3$H-thymidine/μg soluble protein 24 hours after addition of the test compounds was examined and the results are shown in Table 2A.

TABLE 2

| Treatment | mean Thymidine incorp/μg protein ± s.d (% control) | p value vs Control | p value vs $10^{-n}$ROH | p value vs $10^{-n}$RA | p value vs $10^{-n}$lino'-DEA |
|---|---|---|---|---|---|
| Control | 2094 ± 140 (100%) | — | — | — | — |
| 2.5 × $10^{-8}$M RA | 2686 ± 72 (128%) | 0.000 | 0.000 | — | — |
| 2.5 × $10^{-8}$M Retinol | 2034 ± 46 (97%) | 0.501 | — | 0.000 | — |
| $10^{-9}$M Dimethyl imidazolidinone | 2003 ± 128 (96%) | 0.373 | — | — | — |
| 2.5 × $10^{-8}$M ROH + $10^{-9}$M Dimethyl imidazolidinone | 2518 ± 102 (120%) | 0.002 | 0.002 | 0.081 | 0.025 | n = 3

$2.5 \times 10^{-8}$M retinoic acid significantly increased keratinocyte thymidine incorporation over both the ethanol control and the $2.5 \times 10^{-8}$M retinol treatment by 28%. $10^{-9}$M dimethyl imidazolidinone had no effect on keratinocyte proliferation on its own. However, the combination of $2.5 \times 10^{-8}$M retinol + $10^{-9}$M dimethyl imidazolidinone significantly increased keratinocyte proliferation over both the ethanol (by 20%) and the $2.5 \times 10^{-8}$M retinol control treatments (by 23%). Dimethyl imidazolidinone and retinol therefore, act synergistically to increase keratinocyte proliferation to levels which closely resemble the stimulatory effect of retinoic acid.

EXAMPLE 3

The Synergistic Increase in Keratinocyte Proliferation Induced By Retinol and Dimethyl Imidazolidinone is Most Effective at ROH:Dimethyl Imidazolidinone Ratios Ranging From 60:1 to 1:160

In order to determine the range of retinol:dimethyl imidazolidinone ratios which were most effective at enhancing the benefit of retinol, the effect on incorporation of $^3$H-thymidine/μg soluble protein 24 hours after the addition of retinol and linoleamide-DEA in different ratios of amounts, was examined. These were compared to the effects of retinoic acid at equimolar concentrations (with respect to retinol) and the effects of retinol and dimethyl imidazolidinone alone and the results are presented in Table 3A.

Retinoic acid treatment acted as positive control and all concentrations of retinoic acid tested, i.e., $2.5 \times 10^{-7}$M, $2.5 \times 10^{-8}$M and $2.5 \times 10^{-9}$M, significantly increased keratinocyte proliferation over both the ethanol control and each of the $2.5 \times 10^{-7}$M, $2.5 \times 10^{-8}$M and $2.5 \times 10^{-9}$M retinol treatments. Five combinations of retinol and linoleamide were examined with retinol concentrations of $2.5 \times 10^{-7}$M, $2.5 \times 10^{-8}$M and $2.5 \times 10^{-9}$M and dimethyl imidazolidinone concentrations of $10^{-6}$M–$10^{-9}$M. The ratios of retinol:dimethyl imidazolidinone therefore ranged from 60:1 to 1:160 as is illustrated in Table 3B. The synergistic increase indicated in Table 3B is equal to the % control thymidine incorporation of the ROH+dimethyl imidazolidinone treatment which exceeds the combined individual ROH and dimethyl imidazolidinone treatment. All five combinations showed a synergistic increase in thymidine incorporation/soluble protein. The increased cell proliferation was statistically significant. The trend is clear—combinations of retinol and dimethyl imidazolidinone at ratios ranging from at least 60:1 through 1:160 synergistically increase keratinocyte cell proliferation.

TABLE 3A

| Treatment | mean Thymidine incorp/μg protein ± s.d (% control) | p value vs Control | p value vs $10^{-n}$ROH | p value vs $10^{-n}$RA | p value vs $10^{-n}$ imidaz |
|---|---|---|---|---|---|
| Control | 2094 ± 140 (100%) | — | — | — | — |
| 2.5 × $10^{-7}$M RA | 2475 ± 116 (118%) | 0.005 | 0.032 | — | — |
| 2.5 × $10^{-8}$M RA | 2686 ± 72 (128%) | 0.000 | 0.000 | — | — |
| 2.5 × $10^{-9}$M RA | 2556 ± 80 (122%) | 0.001 | 0.000 | — | — |
| 2.5 × $10^{-7}$M Retinol | 2218 ± 79 (106%) | 0.202 | — | 0.032 | — |
| 2.5 × $10^{-8}$M Retinol | 2034 ± 46 (97%) | 0.501 | — | 0.000 | — |
| 2.5 × $10^{-9}$M Retinol | 1977 ± 19 (94%) | 0.203 | — | 0.000 | — |
| $10^{-6}$M Dimethyl imidazolidinone | 1892 ± 119 (90%) | 0.07 | — | — | — |
| $10^{-7}$M Dimethyl imidazolidinone | 2260 ± 166 (108%) | 0.157 | — | — | — |
| $10^{-9}$M Dimethyl imidazolidinone | 2003 ± 128 (96%) | 0.373 | — | — | — |
| 2.5 × $10^{-7}$M ROH + $10^{-6}$M Dimethyl imidazolidinone | 2426 ± 76 (116%) | 0.007 | 0.027 | 0.569 | 0.003 |
| 2.5 × $10^{-8}$M ROH + $10^{-6}$M Dimethyl imidazolidinone | 2565 ± 26 (122%) | 0.001 | 0.000 | 0.052 | 0.001 |
| 2.5 × $10^{-8}$M ROH + $10^{-9}$M Dimethyl imidazolidinone | 2518 ± 102 (120%) | 0.002 | 0.002 | 0.081 | 0.025 |
| 2.5 × $10^{-9}$M ROH + $10^{-6}$M Dimethyl imidazolidinone | 2397 ± 96 (114%) | 0.013 | 0.002 | 0.091 | 0.005 |
| 2.5 × $10^{-9}$M ROH + $10^{-7}$M Dimethyl | 2667 ± 172 (127%) | 0.001 | 0.002 | 0.366 | 0.042 |

TABLE 3A-continued

| Treatment | mean Thymidine incorp/μg protein ± s.d (% control) | p value vs Control | p value vs $10^{-n}$ROH | p value vs $10^{-n}$RA | p value vs $10^{-n}$ imidaz |
|---|---|---|---|---|---|
| imidazolidinone | | | | | |
| $2.5 \times 10^{-9}$M ROH + $10^{-9}$M Dimethyl imidazolidinone | 2379 ± 97 (114%) | 0.017 | 0.002 | 0.072 | 0.055 | n = 3

TABLE 3B

| Ratio (ROH:DMI) | Treatment | Thymidine Incorp$^n$ | | | Synergistic Increase |
|---|---|---|---|---|---|
| | | Control | ROH | DMI | |
| 60:1 | $2.5 \times 10^{-8}$M ROH + $10^{-9}$M Dimethyl imidazolidinone | 100%* | 97%* | 96%* | 120%* (20%) |
| 6:1 | $2.5 \times 10^{-9}$M ROH + $10^{-9}$M Dimethyl imidazolidinone | 100%* | 94%* | 96%* | 114%* (14%) |
| 1:2 | $2.5 \times 10^{-7}$M ROH + $10^{-6}$M Dimethyl imidazolidinone | 100%* | 106%* | 90%* | 116%* (10%) |
| 1:16 | $2.5 \times 10^{-8}$M ROH + $10^{-6}$M Dimethyl imidazolidinone | 100%* | 97%* | 90%* | 122%* (22%) |
| 1:16 | $2.5 \times 10^{-9}$M ROH + $10^{-7}$M Dimethyl imidazolidinone | 100%* | 94%* | 108%* | 127%* (19%) |
| 1:160 | $2.5 \times 10^{-9}$M ROH + $10^{-6}$M Dimethyl imidazolidinone | 100%* | 94%* | 90%* | 114%* (14%) | n = 3
*p < 0.05

EXAMPLE 4

Dimethyl Imidazolidinone and Retinyl Palmitate Synergistically Enhanced Keratinocyte Proliferation A. The effect on incorporation of $^3$H-thymidine/μg soluble protein 24 hours after addition of the test compounds was examined and the results are shown in Table 4A.

$2.5 \times 10^{-8}$M retinoic acid increased keratinocyte thymidine incorporation over both the ethanol control and the $2.5 \times 10^{-8}$M retinyl palmitate treatment by 6%. $10^{-7}$M dimethyl imidazolidinone had no effect on keratinocyte proliferation on its own. However, the combination of $2.5 \times 10^{-8}$M retinyl palmitate + $10^{-7}$M dimethyl imidazolidinone significantly increased keratinocyte proliferation over both the ethanol (by 10%) and the $2.5 \times 10^{-8}$M retinyl palmitate control treatments (by 13%). Dimethyl imidazolidinone and retinyl palmitate therefore, act synergistically to increase keratinocyte proliferation.

B. The effect on TG1 in response to treatment with retinyl palmitate and dimethyl imidazolidinone was examined and the results are shown in Table 4B.

TABLE 4A

Effect of Retinyl Palmitate and Dimethyl Imidazolidinone on Keratinocyte Thymidine Incorporation

| Treatment | mean Thymidine incorp/μg protein ± s.d (% control) | p value vs Control | p value vs $10^{-n}$RP | p value vs $10^{-n}$RA | p value vs $10^{-7}$ DMI |
|---|---|---|---|---|---|
| Control | 3477 ± 258 (100%) | — | — | — | — |
| $2.5 \times 10^{-8}$M RA | 3691 ± 205 (106%) | 0.098 | 0.082 | — | — |
| $2.5 \times 10^{-8}$M Retinyl Palmitate (RP) | 3386 ± 326 (97%) | 0.526 | — | 0.082 | — |
| $10^{-7}$M Dimethyl imidazolidinone (DMI) | 3214 ± 128 (92%) | 0.112 | — | — | — |
| $2.5 \times 10^{-8}$M RP + $10^{-7}$M Dimethyl imidazolidinone | 3812 ± 95 (110%) | 0.050 | 0.069 | 0.377 | 0.001 | n = 3

TABLE 4B

Effect of Retinyl Palmitate and Dimethyl
Imidazolidinone on Keratinocyte TGase Levels

| Treatment | mean TgASE ± s.d (% control) | p value vs Control | p value vs $10^{-8}$RP | p value vs $10^{-6}$DMI |
|---|---|---|---|---|
| Control | 1.00 ± 0.289 (100%) | — | 0.130 | 0.268 |
| 2.5 × $10^{-8}$M RA | 0.155 ± 0.098 (16%) | 0.001 | 0.001 | 0.001 |
| 2.5 × $10^{-8}$M Retinyl palmitate (RP) | 0.790 ± 0.387 (79%) | 0.001 | — | 0.001 |
| $10^{-8}$M dimethyl imidazolidinone (DMI) | 0.990 ± 0.251 (99%) | 0.759 | 0.001 | — |
| 2.5 × $10^{-8}$M RP + $10^{-8}$M dimethyl imidazolidinone | 0.574 ± 0.284 (57%) | 0.001 | 0.001 | 0.001 | n = 3

$2.5 \times 10^{-8}$M retinoic acid was the most effective treatment at repressing keratinocyte TG1 levels (to 15% of control level). $2.5 \times 10^{-8}$ retinyl palmitate also repressed TG1 levels to 79% of control levels but not as effective as retinoic acid. $10^{-8}$M dimethyl imidazolidinone on its own had no effect on keratinocyte TG1 levels. However, $2.5 \times 10^{-8}$M retinyl palmitate+$10^{-8}$M dimethyl imidazolidinone repressed keratinocyte TG1 levels to 57% of control level. Dimethyl imidazolidinone and retinyl palmitate therefore, act synergistically to repress keratinocyte differentiation to in a manner analogous to the effect of retinoic acid.

In Examples 1–4, retinoic acid was used as positive control and reference compound against which the other compounds under analysis were compared. Retinoic acid, in a dose dependant manner, increased thymidine incorporation and decreased transglutaminase I levels in skin keratinocytes. In other words, retinoic acid increased keratinocyte proliferation and decreased keratinocyte differentiation. Retinol or retinyl palmitate was significantly less effective than retinoic acid at inhibiting keratinocyte differentiation and completely ineffective at increasing keratinocyte proliferation.

The effect of retinol or retinyl palmitate on cultured keratinocytes can be enhanced to levels approaching those of retinoic acid by combining retinol or retinyl palmitate with dimethyl imidazolidinone which exerts little or no benefit on their own.

Dimethyl imidazolidinone acts synergistically with retinol or retinyl palmitate both to increase keratinocyte proliferation and decrease keratinocyte differentiation, mimicking the effect of retinoic acid.

EXAMPLE 5

This example illustrates a high internal phase water-in-oil emulsion incorporating the inventive composition.

|  | % w/w |
|---|---|
| Retinol | 0.5 |
| Fully hydrogenated coconut oil | 3.9 |
| 1,3-dimethyl-2-imidazolidinone | 0.2 |
| Brij 92* | 5 |
| Bentone 38 | 0.5 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 6

This example illustrates an oil-in-water cream incorporating the inventive composition.

|  | % w/w |
|---|---|
| Retinol | 0.15 |
| Mineral oil | 4 |
| 1,3-dimethyl-2-imidazolidinone | 1 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 7

This example illustrates an alcoholic lotion incorporating the composition according to the invention.

|  | % w/w |
|---|---|
| Retinyl palmitate | 0.15 |
| 1,3-dimethyl-2-imidazolidinone | 0.1 |
| Ethanol | 40 |
| Perfume | qs |
| Butylated hydroxy toluene | 0.01 |
| Water | to 100 |

EXAMPLE 8

This example illustrates another alcoholic lotion containing the inventive composition.

|  | % w/w |
|---|---|
| Retinol | 0.15 |
| 1,3-dimethyl-2-imidazolidinone | 0.01 |
| Ethanol | 40 |
| Antioxidant | 0.1 |
| Perfume | qs |
| Water | to 100 |

EXAMPLE 9

This example illustrates a suncare cream incorporating the composition of the invention:

| | % w/w |
|---|---|
| Retinol | 0.01 |
| 1,3-dimethyl-2-imidazolidinone | 0.2 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 10

This example illustrates a non-aqueous skin care composition incorporating the inventive combination.

| | % w/w |
|---|---|
| Retinyl palmitate | 0.15 |
| 1,3-dimethyl-2-imidazolidinone | 1 |
| Silicone gum SE-30[1] | 10 |
| Silicone fluid 345[2] | 20 |
| Silicone fluid 344[3] | 55.79 |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[1] A dimethyl silicone polymer having a molecular weight of at least 50,000 and a viscosity of at least 10,000 centistokes at 25° C., available from GEC
[2] Dimethyl siloxane cyclic pentamer, available from Dow Corning Corp.
[3] Dimethyl siloxane tetramer, available from Dow Corning Corp.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin conditioning composition comprising:
   (a) from about 0.001% to about 10% of a compound selected from the group consisting of retinol and a retinyl ester;
   (b) from about 0.001% to about 10% of dimethyl imidazolidinone; and
   (c) a cosmetically acceptable vehicle.

2. The composition of claim 1 wherein the retinyl ester is selected from the group consisting of retinyl palmitate, retinyl acetate, retinyl propionate, and mixtures thereof.

3. The composition of claim 1 wherein the ratio of ingredient (a) to ingredient (b) is in the range of from about 60:1 to about 1:160.

4. A method of conditioning skin the method comprising applying topically to skin the composition of claim 1.

5. A method of mimicking the effect on skin of retinoic acid, the method comprising applying to the skin the composition of claim 1.

* * * * *